United States Patent [19]

Magee et al.

[11] 4,302,754
[45] Nov. 24, 1981

[54] WEAR PARTICLE DISINTEGRATOR MONITOR

[75] Inventors: James H. Magee, Palmyra, N.J.; Thomas E. Tauber, Lansdowne, Pa.

[73] Assignee: Technical Development Co., Glenolden, Pa.

[21] Appl. No.: 11,553

[22] Filed: Feb. 12, 1979

[51] Int. Cl.³ .................... G01R 33/12; G08B 21/00
[52] U.S. Cl. .................. 340/631; 200/61.09; 210/223; 235/92 PC; 324/204; 324/235; 340/526; 340/627
[58] Field of Search ............... 340/526, 627, 631, 682; 324/204, 213, 235; 200/61.09; 235/92 PC; 210/223

[56] References Cited

U.S. PATENT DOCUMENTS

| | | | |
|---|---|---|---|
| 3,259,891 | 7/1966 | Coulter et al. | 340/627 |
| 3,748,576 | 7/1973 | Sigournay | 340/631 X |
| 3,920,961 | 11/1975 | Berg | 235/92 PC |
| 4,070,660 | 1/1978 | Tauber | 200/61.09 X |
| 4,100,491 | 7/1978 | Newman, Jr. et al. | 340/631 X |
| 4,219,805 | 8/1980 | Magee et al. | 340/631 |

Primary Examiner—John W. Caldwell, Sr.
Assistant Examiner—Joseph E. Nowicki
Attorney, Agent, or Firm—Robert S. Lipton

[57] ABSTRACT

An electromagnetic system is provided to monitor the activity of a ferrous debris detector of the type which uses electric discharges to automatically disintegrate magnetically concentrated accumulations of micron sized wear particles in hydraulic systems. The data provided are used to detect instances of abnormal wear as shown by either an unusually large number of such discharges or an excessive rate of discharge. Where such abnormality occurs the monitor will provide an audiovisual alarm to warn of the problem in time to prevent catastrophic failure of the system.

7 Claims, 5 Drawing Figures

WEAR PARTICLE DISINTEGRATOR MONITOR

BACKGROUND OF THE INVENTION

1. Field of the Invention

The present invention relates to the automatic display and interpretation of the operations of a ferrous debris detector of the type which generates pulses of electricity to disintegrate magnetically concentrated accumulations of 0 to 10 micron sized wear particles in hydraulic systems.

2. Description of the Prior Art

One characteristic of heavily loaded mechanical systems, such as helicopter transmissions and rotor gear boxed which are lubricated by pressurized circulating oil streams, is the generation of some quantity 0 –10 micron sized particles by the constitutent parts as they wear in service. The particles of "fuzz" are picked up and circulate throughout the oil system with pumped oil. In addition where system overloads which lead to chipping of mating parts, such as gear teeth, or excessive vibration leading to the initiation of fatigue cracks occur, larger particles, having diameters of 100 microns will start to appear. If these conditions are allowed to progress without being detected and checked, catastrophic failure may result in service.

There exist today a large number of devices for the purpose of removing and analyzing potentially harmful debris particles from pressurized hydraulic systems. These may be filtering devices for varying complexity such as that shown by Miller and Rumberger in U.S. Pat. No. 3,878,103 or cyclonic devices shown as those shown by Schulze in U.S. Pat. No. 3,129,173 and Martin in U.S. Pat. No. 3,528,552. Where ferrous particles are involved such devices often include a magnet to aid in attracting and capturingthese particles. A wide variety of such devices exist ranging from fairly simple units similar to that shown by Botstiber in U.S. Pat. No. 2,936,890 to more complex combination filter and magnet systems such as those shown by Botstiber in U.S. Pat. No. 3,317,042, Winslow in U.S. Pat. No. 3,127,255, Patton in U.S. Pat. No. 2,980,257 and Lammers in U.S. Pat. No. 3,421,627.

Many of these devices provide a dynamic, positive means for monitoring system status by signalling the arrival and capture of one or more particles. Such signalling systems are shown by Botstiber in U.S. Pat. Nos. 3,432,750 and 3,317,042, Booth in U.S. Pat. No. 2,462,715 and Bourne in U.S. Pat. No. 2,450,630. These systems have found wide use in many types of helicopter engines and transmission systems. It should be noted, however, that in most applications it is usually felt to be unnecessary to announce the capture of individual fuzz particles since there are, relatively speaking, quite a large number of them. Also their small size makes them comparatively innocuous as long as they are freely moving in the system. Therefore, a regularly scheduled cleanup of the magnet is about all that is normally needed when fuzz is the only contaminent present.

On the other hand, if particles in excess of 100 microns start to appear it is most important that the pilot or operator be altered to each of them as they arrive since the number of such particles captured and their rate of arrival will provide an early warning of cracking or impending fatigue failure somewhere in the system. When these events occur, accelerated maintenance must be scheduled to find and repair the affected areas if catastrophic failure is to be avoided. This signal discrimination is normally done by using either an insulated screen type filter or a electric chip detector which is connected to an alarm. It is only when the wires in the screen or the magnet poles are bridged by "large" particles that the alarm will sound. The pole gap or screen openings are, in theory, large enough for fuzz particles to pass through and therefore not trigger the alarm. In practice, however, it is sometimes found that particles of fuzz will also tend to collect around the openings and agglomerate to the point where they too will bridge them and generate an alarm. In most state-of-the-art devices there is usually no way short of stopping the engine and visually examining the detector to determine if such an alarm is spurious or not. While spurious signals do not require a more extensive tear down inspection, as would a real one, they obviously tend to seriously impede the efficient, continuing use of the system.

There is available today one type of detector system which attempts to prevent this problem. In this system, which is described by Tauber in U.S. Pat. No. 4,070,660, the material bridging the gap is subjected to a pulse of current. This acts to disintegrate fuzz agglomerates and break the electrical alarm circuitwhile leaving large particles and therefore the alarm circuit unaffected. Such a system has been found to be quite successful in reducing the number of unscheduled maintenance operations. However, as experience has been gained with this type of detector it has been found that a knowledge of fuzz buildup can often provide valuable information as to the degree and nature of the wear being experienced by the hydraulic system and the components operating in it. Thus, in a properly aligned and loaded gear train, for example, a specific rate and pattern of wear particle generation, defined more or less as "normal", can be expected. Where there are problems with improper alignments or system overloads, or where gears and other mating parts show defects, one would then expect to find non-specific or "abnormal" particle generation rates and patterns. It has been found that in a pulse type of system, as described above, keeping track of the number and/or rate of "successful" discharges can provide useful data as to rate and pattern "normality". Thus, when either a predetermined number of discharges is reached or rate/unit time exceeds a predetermined level an appropriate alarm can be sounded to call attention to the problem. By so doing proper maintenance can be scheduled without having to unnecessarily abort the operation of the system.

SUMMARY OF THE INVENTION

The subject invention is intended to enhance the utility of ferrous debris detectors used in hydraulic and lubrication systems such as are used in helicopter engines and rotor gear boxes. In particular it is an adjunct to a particular type of detection system, which after capturing debris particles of such a size that the gap between the poles of a doubled poled magnet is closed, tests the nature of debris by discharging a capacitor so as to cause a pulse current to flow through it. In this system if the debris is merely an agglomeration of relatively harmless 0 –10 micron sized wear particles held together by mutual magnetic attraction, the pulse will break them up and clear the gap. Should, however, the debris consist of one or more 100 + micron sized particles of a type typically originating from a growing fatigue crack, the pulse will not destroy them and thus will not clear the gap. When this happens an alarm is given to the pilot to abort the flight as soon as possible to prevent a catastrophic failure. Thus, as presently configured, the system effectively discriminates between innocuous collections of fuzz indicating wear in the system and more serious large debris particles indicating fatigue cracking and provides an appropriate warning whenever the latter situation occurs.

In using such a system it has also been found that a detailed knowledge of the rate of wear particle generation can provide very useful data so to the overall condition and performance of the operating system. Thus, in a new system, large numbers of such particles can be expected as the system "wears-in". In time, as rough spots are worn away, the rate of generation will decline if the system components are properly aligned and loaded, until it reaches some steady state value. This change in generation rate is also tracked by a decreasing number of capacitor discharges and a slowing of the rate at which they occur. Should, however, overloads in use, misalignments of system components, or materials problems such as improper heat treatment of mating parts cause accelerated wear, the rate of generation and therefore the number and rate of capacitor discharges would not decrease at the same rate. In extreme cases, these factors probably would even increase up to or beyond that observed during initial break-in. The subject invention is intended to provide more precise knowledge as to the existence and magnitude of these conditions. It does this by counting the capacitor discharge pulses and computing a rate per unit time as the system operates. In use, the count and rate data are provided to the operator directly as analog or digital readouts and/or by triggering an alarm whenever preset count or rate values are exceeded. By so doing it will be possible to alert the operator to the existence of an abnormal wear situation and allow an assessment of the nature and degree of damage experienced. With these data it will then be possible to estimate residual service life and to schedule maintenance operations more effectively than is now possible.

It is the object of this invention to provide a ferrous particle detection system for use in circulating liquid media systems of the type which uses electric pulses to discriminate between agglomerations of small wear particles and individual large particles indicative of fatigue cracks wherein the generation and accummulation of the wear particles is monitored.

It is a further object of the invention to provide signals suitable for analog or digital display which are indicative of the number of electric pulses generated.

It is still another object of the invention to provide a means for alterting the operator that an excessive number of discharges indicative of accelerated wear in the system has occurred.

It is yet another object of the invention to provide means for computing the rate at which discharges occur for more positive assessment of system damage.

It is still a further object to provide display means indicative of the discharge rate and capable of alterting the operator whenever the rate reaches excessive levels.

Other and further objects of this invention will become apparent to those skilled in the art upon consideration of the following specification when read in conjunction with the attached drawings.

DESCRIPTION OF THE PREFERRED EMBODIMENT

Figure 1:
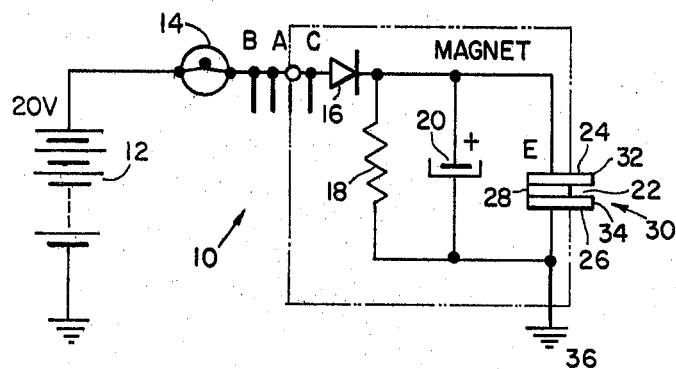
FIG. 1 is a circuit diagram of a basic wear particle detector and capacitive discharge system wherein discharges are automatically initiated.
Figure 2:
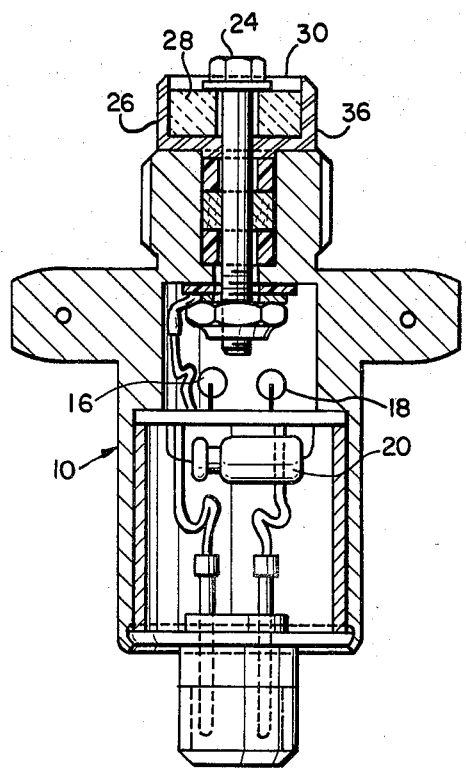
FIG. 2 shows, in front elevation a basic wear particle detector device equipped with the required component parts for the device of FIG. 1.

Referring now to FIGS. 1 and 2 we see the basic organization and structure of a magnetic particle detector/capacitive discharge system 10 of the type to which the subject invention is to be attached. For a better understanding of the total system the next paragraphs will describe the basic particle detector/capacitive discharge system and how it operates.

Typically, such a system will consist of a DC power source 12, such as a battery. The positive pole of the battery is connected through indicator light 14 and diode 16 to the main operating components of the system. These consist of a parallel connected high resistance bleeder resistor 18, capacitor 20 and magnetic circuit 22. Circuit 22 itself contains two electrodes 24 and 26. These are generally the pole pieces of an electromagnet in which case they are permanently magnetized with opposite polarity with respect to each other and electrically insulated from each other through insulator 28. This may consist of a permanent magnet of an electrically nonconductive material such as bonded ferrite ($Fe_3O_4$). The electrodes and insulator are arranged to form an operational gap 30 of a specific, predetermined opening. In use the magnetic faces 32 and 34 which are exposed to the hydraulic fluid with the gap 30 being the reference gap which must be bridged to trigger both a capacitive discharge and a signal from the subject invention.

When installed in a hydraulic or lubrication system the basic detector operates as follows:

When system voltage is applied from battery 12 to the operating components of detector 10, capacitor 20 becomes charged while magnetic circuit 22 becomes energized. Since electrodes 24 and 26 are insulated from each other, no current actuallyflows in the circuit and therefore indicator 14 does not light up. If, however, a ferrous particle is attracted by magnetic insulator 28 and becomes lodged in gap 30 so as to bridge it, a conductive path forms between electrodes 24 and 26 allowing the capacitor to discharge along this path to ground 36. If the particle is really an agglomeration of fuzz particles it will tend to disintegrate under the effects of the capacitor discharge impulse current, causing the fuzz particles and other non-critical particles to disintegrate and go back into the flowing fluid stream. This allows gap 30 to open and capacitor 20 to recharge. If however, the particle is too large to be melted or disintegrated by the capacitor discharge, the gap will not open and the current flowing from battery 12 through the magnetic circuit will cause indicator 14 to light up and indicate the presence of a substantial or critical particle and a potential failure condition. In this system the purpose of diode 16 is to block the capacitor discharge current effects from reflecting back into other parts such as additional detectors installed elsewhere in the aircraft. Furthermore bleeder resistor 18 allows the slow discharge of capacitor 20 when the power source is off. This is provided primarily to prevent damage to other aircraft instrumentation when the unit is removed from maintenance and inspection.

From the electrical point of view the circuitry described above, when operating, can be considered as a random pulse generator, the output of which is variable both as to frequency and duration of occurrence. With suitable logic it is possible to count these pulses to provide the pilot with one measure of the "state of being" readout. In addition it is possible to determine the rate at which the pulses are occurring to provide yet another measure of the way the system is wearing. The invention described herein is designed to provide capabilities for both of these measurements. In order to do this, however, separate circuit elements are necessary. Therefore, to provide greater understanding of the invention, these two functions will be described separately, even though in the preferred embodiment both of them are contained within.

a. Pulse Counting

Figure 3:
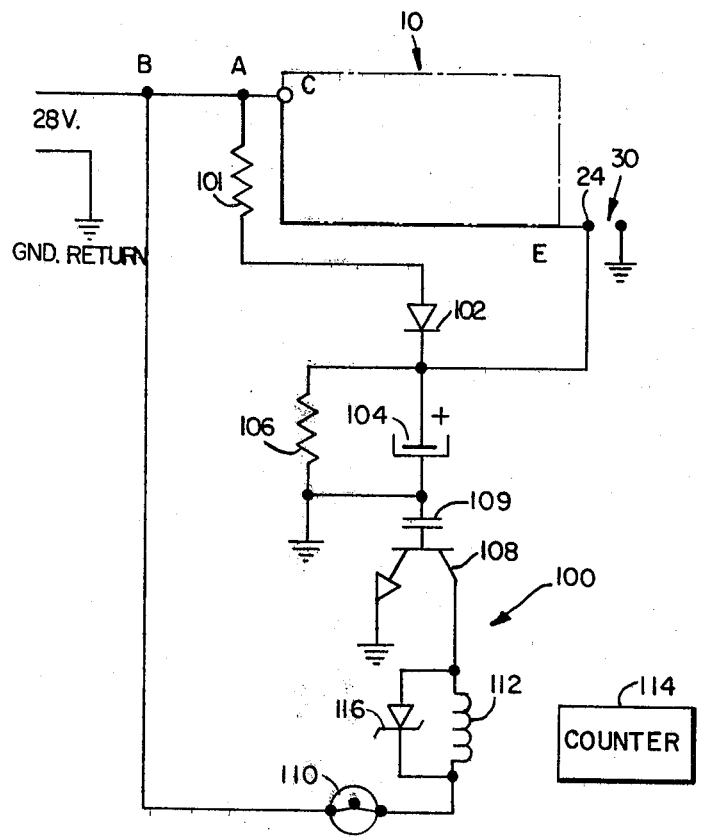
FIG. 3 is a circuit diagram of a modified wear particle detector and capacitive discharge system as shown in FIG. 1 wherein the number of successful discharges are counted.

The pulse counting circuit is displayed in FIG. 3. As shown it is a separate circuit 100 having parallel charging and counting sections. The charging circuit connects to discharge system 10 at point A in the line coming from power source 12. In this case the 28 VDC main helicopter power source is used as compared to a battery shown in FIG. 1. This line feeds, as in system 10, through charging resistor 101 and blocking diode 102 into blocking capacitor 104 and bleeder resistor 106, and as well as plate 24 of magnetic assembly 22 at point E. In this respect this line is a duplicate pulse generator in which current will flow when gap 30 is bridged. However, it serves another purpose as well. When capacitor 104 is fully charged it effectively biases the base of tranistor 108 to cutoff. To keep voltage gains reasonable capacitor 104 works in conjunction with an isolation capacitor 109. Normally this will be much lower in capacitance than capacitor 104.

The counting section which proceeds from point B through time delay 110 and coil 112, the actuator of counter 114, and through transistor switch 108 to ground. As long as gap 30 remains open no counts are registered. However, when gap 30 is closed, capacitor 104 discharges in the same manner as capacitor 20. In so doing switch 108 opens and current flows through it to ground. When the gap reopens, capacitor 104 recharges and after a short interval, reaches a positive voltage sufficient to close the switch and shut off current flow.

Electrically this flow interval has the characteristic of negative going pulse. This is limited and shaped by Zener diode 116 and coil 112 of counter 114 to have 5 V peak and be essentially a negative going square wave with a fairly sharp fall and then rise characteristic. The counter itself is triggered by the positive going rise voltage in coil 120 so it increments upwards by 1 only after a successul disintegration since capacitor 104 can only recharge to close switch 108 if gap 30 opens.

This rising pulse sensitivity, however, creates one problem. When the system is shut off, capacitor 104 will bleed off through resistor 18 in the same manner as capacitor 20. As a result, when the system is turned on, capacitor 104 will be low and switch 108 will open for the short interval of time it takes for capacitor 104 to be recharges. Thus, the counter will perceive a positive going voltage and increment up by 1. To prevent such specious counts, time delay relay switch 110 is incorporated into the counting circuit to hold it open until switch 208 has time to close. Normally this takes less than a second so there is no real effect on the overall operation of the system.

b. Accumulation Rate Measurement

As noted above, a second data valve of interest is the determination of discharge rate in terms of events per some arbitraryunit time. This sends or gives the operator a better feel for state of being of the system being monitored than a simple pulse counting operation.

Figure 4:
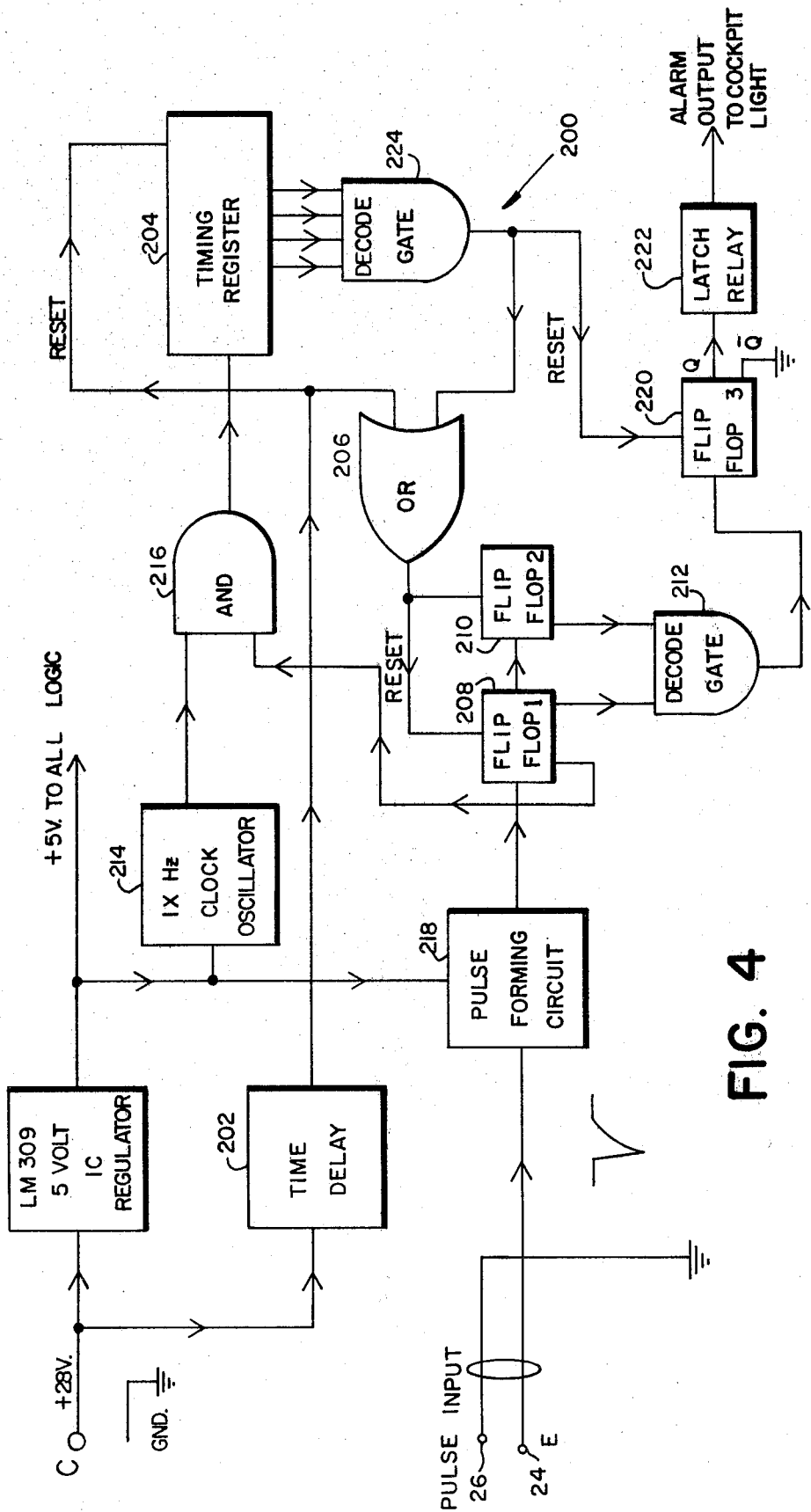
FIG. 4 is a block diagram of a discharge and rate counter for a detector and capacitive discharge system as shown in FIG. 1.

Referring now to FIG. 4 we see a circuit 200 for rate of occurrence determination. As with the pulse counting circuitry this circuit is in parallel with the basic system circuitry. As configured it contacts the system power supply 16 at point C and at plate 24 of magnetic circuit 22, as shown in FIG. 1.

In operation it senses the occurrence of discharge pulses as gap 30 is closed by one or more particles as follow:

When system 200 is turned on, time delay 202 is activated. This time delay serves a different purpose from that in the pulse counting circuit. That is instead of shutting off the system until capacitor 20 charges up and the pulsing circuit is stable, it sets a reset line which initially zeros out timing register 204 and, through OR gate 206, sets first flip flop 208 and second flip flop 210 to Q̄. Under these conditions the flip flops feed an output code of "00" into first decode gate 212. At the same time the system 10 is activated 1 KHZ oscillator 214 starts in operation. This feeds timing pulses into AND gate 216 but these cannot reach timing register 204 until flip flop 208 shifts to a Q condition. Such a shift will only occur when a pulse is received from a successful discharge in the same manner as described with pulse counting system 100. This pulse, which may have a spike voltage as high as 25 volts feeds into pulse shaper 218. This reduces the input to 5 V so that it can safely pass into flip flop 208 and cause it to shift to a Q condition. When this is achieved, AND gate 216 opens and timing pulses now reach timer 204. However, flip flop 210 does not shift to a Q so that the output code from the two is not 10. All during this time a third flip flop 220 is also held Q̄ which in turn keeps latch relay 222 locked open thus preventing an alarm signal from being fed to the cockpit. If no second pulse is received before register 204 times out the final output at that time it is decoded by 4 input decode AND gate 220 and sets the flips back to their original condition.

If however, a second pulse is received flip flop 208 shifts back to Q and flip flop 210 shifts to Q giving an output code of 11. This is decoded by input decode AND gate 212 to produce an output which shifts flip flop 220 to close relay 222 and sounds an alarm.

It should be noted that in particular environments, it may be desirable for more than one "unsuccessful" pulse to occur within a stipulated period before the alarm is sounded. That is, the pilot may only be concerned if 3 or 4 or even more pulses occur in some arbitrary time period such as 15 minutes. If the number is 2, then only one timing register 204, as shown in FIG.

4, is required. As described above, the timer is activated by the first pulse and runs until either a second pulse resets it and closes latch relay 222, or the preset time period is exceeded, at which time flip flops 208 and 210 are reset through OR gate 206 to the to the $\bar{Q}$ condition.

If however, the number involved is 3 or more, circuit 200 is not adequate and must be modified. Here, the problem to be solved is one of defining the time period of interest. For example, consider a sequence of events occuring at 0, 14.59, 15.01 and 29.58 minutes. It is apparent that if the reference numeral is 3 and the reference times began at 0 and 15.01 minutes no alarm would be sounded, but if the reference time were set at 14.59 then the 4th pulse would arrive in time to trigger an alarm. To do this it is necessary to keep separate time tracks for each pulse received. A circuit set up to do this in any desired time period is shown as FIG. 5. In this, the selected time period shown is 17 minutes 4 seconds ($2^{10}$ or 1024 seconds to simplify time decoding) and the number of pulses needed to trigger the alarm is 3. However, with suitable logic, any time period could be selected. For a larger number of pulses the basic principles are the same, but the circuit will require N-1 counters where N is the number of events to be counted and other suitable modifications to accommodate them.

Figure 5:
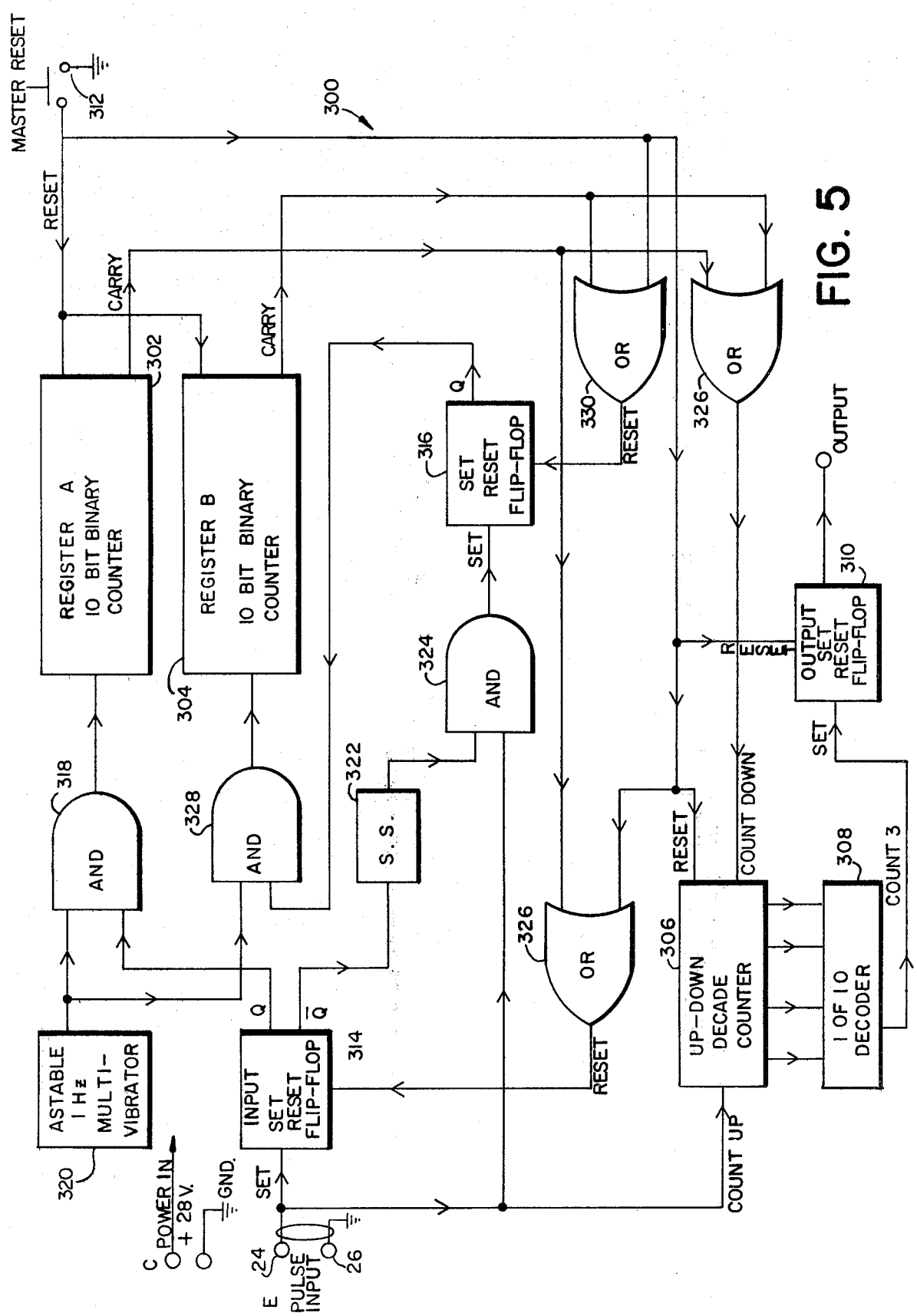
FIG. 5 is a block diagram of a modified rate counting circuit.

Referring now in detail to FIG. 5 we see multiple pulse alarm circuit 300. The general principle of operation is that a third event or pulse will cause up/down decode counter 306 to advance to a count of 3. This, when decoded by "1 of 10" decoder 308 sets the output of set/reset flip flop 310 to provide a final alarm output. As noted, the circuit as configured in FIG. 5 has a time period of 17 minutes, 4 seconds.

In use, the circuit is activated either by time delay 202 as shown in FIG. 4, or by master manual switch 312. Whichever method is used, the output pulse provided acts to reset counters 302, 304 and 306 to 0 and flip flops 310, 314 and 316 to $\bar{Q}$. When a first pulse is received, input flip flop 314 is set to Q, which when fed into AND gate 318 allows pulses at frequcency of 1 Z from astable multivibrator 320 to be counted by 10 bit binary counter 302. At the same time up/down counter 306 counts up from 0 to 1. Flip flop 316 is not affected by the change from $\bar{Q}$ to Q in flip flop 314. This is because the set pulse is delayed in single shot 322. Thus, the input pulse is over before the second input to AND gate 324 goes high. As a result, only one of the two inputs to AND gate 324 is high and therefore the output will stay low and not set flip flop 316. However, one input to AND gate 324 is now high and in effect the gate is now primed.

If a second event or pulse does not occur during the 1024 second count in counter 302, the carry pulse (the 1025th pulse) coming from the counter will act to reset flip flop 314 through OR gate 326 and cause counter 306 to go back to 0 with a count down pulse from OR gate 326.

On the receipt of a second pulse within the 1024 second limit, input flip flop does not reset $\bar{Q}$, so single shot 322 does not retrigger. As a result, both inputs to AND gate 324 go high, flip flop is set to Q and AND gate 328 is set to admit 1 H Z pulses to counter 304. At the same time, counter 306 advances to a count of 2. If a third pulse is received while both of counters 302 and 304 are operating, counter 306 will output a count of 3 pulse which sets out put flip flop 310, which in turn activates the alarm. The alarm can only be stopped by resetting the whole system by master preset switch 312.

If, however, a third pulse is not received before the first 1024 second interval expires, counter 302 times out and the carry pulse resets flip flop 314 to $\bar{Q}$ and causes counter 306 to count down from 2 to 1 as described herein above. Similarly, if counter 304 times out to 1025 the carry pulse resets flip flop 316 through OR gate 330 and provides a count down pulse to reset counter 306 to 0. The next pulse received will start the whole sequence as described above over again. On the other hand, if a third pulse is received before counter 304 times out, it will act to reactivate counter 302 and advance counter 306 back to 2. Thus, the circuit keeps a running track of the number of events in any period of 1024 seconds, so that if 3 events occur in that period, an alarm will be sounded.

While the wear particle disintegrator monitor has been described with reference to a preferred embodiment, it is to be understood that various changes and modification may be made within the scope and spirit of the invention.

What is claimed is:

1. An apparatus for the attraction, collection and destruction of wear particles in fluid systems and adapted to provide output information on apparatus performance comprising:
   a wear particle detector means for generating wear particle signals representative of critical particle size and non-critical particle size, respectively,
   said wear particle detector means including a digital pulse generation means for generating said wear particle signals as digital pulses whenever a wear particle of non-critical size is destroyed; and
   a counting means adapted to be connected to said digital pulse generation means to keep a record of the number of said digital pulses.

2. The apparatus as defined in claim 1 wherein said wear particle detector means is adapted to be connected to an electric power source and further comprises:
   a pair of electrodes of electrically and magnetically conductive materials spaced apart so as to form an operational gap of predetermined dimensions and thereby constituting a discontinuity of an energized electric indicating circuit adapted to attract and collect wear particles;
   a means to provide a magnetic field between said electrodes:
   a capacitor connected in parallel with said operational gap so as to cause a release of the charge on said capacitor through a particle or aggregation of particles of such size as to close the electric circuit, said released charge being of sufficient magnitude to disintegrate non-critical size particles, thus causing said circuit to reopen and said capacitor to recharge;
   alarm means connected to said capacitor and activated whenever said capacitor discharge fails to destroy a wear particle so that said electric circuit remains closed to generate said wear particle signal representing a critical size particle;
   suppression means for preventing transients resulting from said discharge from affecting other parts of the wear detector which includes a power source and means for transmitting said power to the capacitor and said electrodes; and
   bleeder means for the gradual discharging of said capacitor whenever said power source is turned off.

3. The invention according to claim 2 wherein said digital pulse generation means comprises:
- a circuit parallel to said electric circuit adapted to detect the opening of said electrical circuit, said parallel circuit being adapted to generate said digital pulses in response to said release of the charge on said capacitor and subsequent capacitor recharge for use with said counting means to record the number of wear particle disintegrations.

4. The invention of claim 3 wherein said counting means comprises:
- a positive sensing digital meter adapted to sense and count said digital pulse upon recharging of said capacitor after the disintegration of a wear particle; and
- time delay means to prevent spurious event counts resulting from pulses generated from the capacitor recharging after being discharged by said bleeder means from reaching said meter.

5. The invention of claim 4 wherein said meter comprises a timing means operably connected thereto adapted to determine the rate of which capacitor discharges and recharges are occurring in a given period of time.

6. The invention of claim 5 wherein said timing means comprises an oscillator adapted to emit timing pulses whenever said capacitor discharges and recharges, said timing pulse being adapted to being counted by an integral timing count register for a preselected period of time, said timing means being further adapted to activate a second alarm means if a second capacitor discharge and recharge occurs while said timing count register is still counting said timing pulses.

7. The invention of claim 5 wherein said timing means comprises:
- a plurality of integral timing count registers operably connected to said meter and adapted to allow the delay of alarm activation until a preselected number of capacitor recharges occur within said preselected time whereby a separate counter is used to record the time which elapses from when each capacitor recharge occurs and further including means for operably connecting said registers for receiving a signal indicative of capacitor recharge; and
- event counting means adapted to determine at any time how many of said counters are in operation so that if N-1 counters, where N is the preselected number of charges to activate said alarm, are counting when the Nth recharge occurs, said alarm means is activated.

* * * * *

UNITED STATES PATENT AND TRADEMARK OFFICE
CERTIFICATE OF CORRECTION

PATENT NO. : 4,302,754
DATED : 11/24/81
INVENTOR(S) : Thomas E. Tauber and James Magee It is certified that error appears in the above-identified patent and that said Letters Patent are hereby corrected as shown below:

Column 8, line 47, delete the punctuation of a colon [:] and insert in its stead the punctuation of a semicolon ;.

Signed and Sealed this

Seventh Day of December 1982

[SEAL]

Attest:

Attesting Officer

GERALD J. MOSSINGHOFF
Commissioner of Patents and Trademarks